United States Patent [19]

Hasegawa

[11] 4,447,456
[45] May 8, 1984

[54] **STRAIN OF *CORYNEBACTERIUM FASCIANS* AND USE THEREOF TO REDUCE LIMONOID BITTERNESS IN CITRUS PRODUCTS**

[75] Inventor: Shin Hasegawa, Pasadena, Calif.

[73] Assignee: The United States of America as represented by the Secretary of Agriculture, Washington, D.C.

[21] Appl. No.: 456,954

[22] Filed: Jan. 10, 1983

[51] Int. Cl.$^3$ ............................ A23L 1/00; C12R 1/15
[52] U.S. Cl. ...................................... 426/51; 435/843; 426/52
[58] Field of Search ....................... 426/51, 52, 49, 61; 435/253, 267, 843

[56] References Cited

U.S. PATENT DOCUMENTS

| | | | |
|---|---|---|---|
| 3,869,345 | 3/1975 | Hasegawa et al. | 195/62 |
| 3,911,103 | 10/1975 | Hasegawa et al. | 426/51 |
| 3,917,512 | 11/1975 | Hasegawa et al. | 195/62 |
| 3,920,851 | 11/1975 | Hasegawa et al. | 426/51 |

OTHER PUBLICATIONS

S. Hasegawa, M. N. Patel and R. C. Snyder, "Reduction of Limonin Bitterness in Navel Orange Juice Serum with Bacterial Cells Immobilized in Acrylamide Gel," *Journal of Agricultural and Food Chemistry*, vol. 30, pp. 509–511 (1982).

B. Vaks and A. Lifshitz, "Debittering of Orange Juice by Bacteria Which Degrade Limonin," *Journal of Agricultural and Food Chemistry*, vol. 29, pp. 1258–1261 (1981).

W. L. Stanley and A. C. Olson, "Symposium: Immobilized Enzymes in Food Systems," *Food Science*, vol. 39, pp. 660–666 (1974).

A. C. Olson and R. A. Korus, "Immobilized Enzymes," *Enzymes in Food and Beverage Processing*, ACS Symposium Series No. 47, Ed by Ory and Angelo, American Chemical Society, pp. 100–131 (1974).

*Manual of Clinical Microbiology*, 2nd edition, Eds. Linnette, Spaulding and Truent, American Society for Microbiology, Washington, D.C. (1974).

Bergey's *Manual of Determinative Bacteriology*, 8th Editions Eds. Buchanan and Gibbons; Williams and Wilkins, Baltimore, MD (1974).

*Primary Examiner*—Joseph M. Golian
*Assistant Examiner*—Marianne S. Minnick
*Attorney, Agent, or Firm*—M. Howard Silverstein; David G. McConnell; Margaret A. Connor

[57] ABSTRACT

Bitterness in limonoid-containing citrus juice is reduced by treatment with a novel strain of *Corynebacterium fascians* having the capability of producing enzymes for metabolizing limonoids without the presence of a limonoid inducer in the growth medium.

15 Claims, 1 Drawing Figure

STRAIN OF *CORYNEBACTERIUM FASCIANS* AND USE THEREOF TO REDUCE LIMONOID BITTERNESS IN CITRUS PRODUCTS

BACKGROUND OF THE INVENTION

1. Field of the Invention

The invention is related to and has among it objects a novel bacterial strain and use thereof to reduce limonoid bitterness in citrus products and by-products, particularly citrus juices.

2. Description of the Prior Art

Bitterness due to limonoids in certain citrus juices is one of major problems of the citrus industry worldwide and has significant economic impact. At least 29 limonoids have been isolated from citrus and citrus hybrids; four of them, limonin, nomilin, ichangin and nomilinic acid, are bitter. Limonin is the principal bitter limonoid constituent of citrus juice and the primary cause of the bitterness problem. Because of its intense bitterness, only a small amount of limonin is needed to render the juice unpalatable. Recently, nomilin has been shown to also cause the bitterness problem in certain juices.

The intact fruit does not normally contain limonin, but rather a nonbitter precursor, limonoate A-ring lactone. This precursor converts to limonin in the juice soon after extraction. This conversion proceeds under acidic conditions and is also accelerated by the action of limonin D-ring lactone hydrolase which has been shown to be present in citrus. This phenomenon of delayed bitterness is a serious economic problem to the citrus industry and many methods to prevent or remove limonin bitterness have been tried, including treatment of the fruit with ethylene gas, selective adsorption of limonin from juice using cellulose acetate beads, and use of limonin bitterness suppressing agents in the juice. None of these methods has proved entirely satisfactory.

Several species of bacteria capable of metabolizing limonoids have been isolated and treatment of citrus juice with limonoid-metabolizing bacteria or enzymes isolated from such bacteria has been carried out to reduce limonin bitterness. Hasegawa et al., *Journal of Agricultural and Food Chemistry*, Volume 30, pp 509-511 (1982) describes limonin debittering of naval orange juice using *Arthrobacter globiformis* cells cultured on a nutrient medium containing sodium limonoate and subsequently immobilized in acrylamide gel. Vaks and Lifshitz, *Journal of Agricultural Chemistry*, Volume 29, pp 1258-1261 (1981) discloses the use of *Acinetobacter* sp. cultured on a medium containing limonin to debitter orange juice. Their treatment methods included use of the free cells, immobilization of the cells in acrylamide or agarose and entrapment in a dialysis sac. U.S. Pat. Nos. 3,869,345 and 3,911,103 (Hasegawa et al.) disclose the preparation of the enzyme, limonoate dehydrogenase from *Arthrobacter globiformis* cultured on a nutrient medium containing limonoate and use of the enzyme to reduce the development of bitterness in citrus products containing the limonin precursor, limonoate A-ring lactone. U.S. Pat. Nos. 3,917,512 and 3,920,851 (Hasegawa et al.) disclose preparation of the enzyme, limonoate:NAD(P) oxidoreductase from Pseudomonas sp. 321-18 cultured on a nutrient medium containing limonoate and use of the enzyme to debitter citrus products.

The primary disadvantage of the previously-isolated limonoid-metabolizing bacteria is that they all require the presence of a limonoid inducer in their growth media to produce cells which possess limonoid-metabolizing enzymes. Presently, no commercial source of citrus limonoids exists, thus production of bacterial cells for metabolizing limonoids is difficult, time-consuming and costly.

SUMMARY OF THE INVENTION

I have discovered a new and unusual strain of the bacterium *Corynebacterium fascians* which produces constitutive enzymes (enzymes formed without exogenous induction) for limonoid metabolism and which is capable of reducing limonoid bitterness in citrus products.

In accordance with this discovery, it is an object of the invention to provide a new and useful bacterium which produces bacteria cells capable of metabolizing enzymes without the need for the presence of a limonoid inducer in the growth medium. Since the requirement for a limonoid inducer is eliminated and the bacterium can be grown on relatively inexpensive carbon sources, production of it is more economical and convenient than production of previously-known limonoid-metabolizing bacteria.

It is also an object of the invention to provide a method of use of the novel strain to reduce limonoid bitterness in citrus products, and by-products, particularly citrus juices. Isolation of the limonoid-metabolizing enzymes produced by *C. fascians* is not required for debittering citrus juice, thus the expensive and time-consuming steps of enzyme extraction and purification are eliminated.

Further objects and advantages of the invention will be evident from the ensuing description wherein parts and percentages are by weight unless specified. The abbreviation "ppm" used herein refers to parts per million.

DETAILED DESCRIPTION OF THE INVENTION

Figure 1:
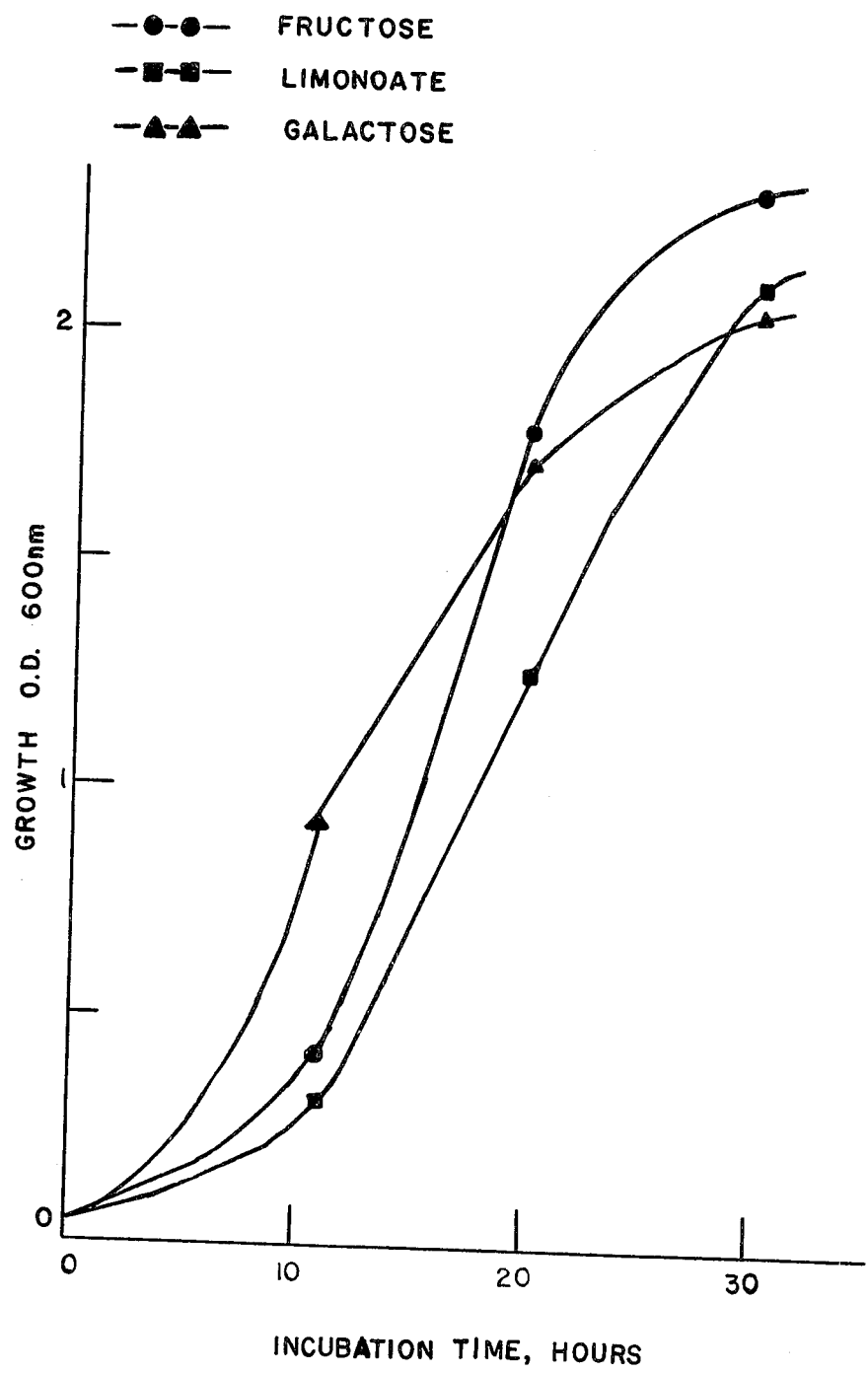
FIG. 1 shows growth curves of *C. fascians* grown on various carbon sources.

The invention comprises a novel *Corynebacterium fascians* bacterium which produces constitutive enzymes for the metabolism of limonoids without the presence of a limonoid inducer in the growth medium. Cells of *C. fascians* can effectively convert bitter components in citrus products to nonbitter compounds. For example, the novel bacterium can convert bitter limonin to non-bitter limonol via the 7α-hydroxylimonoid pathway; limonin to non-bitter 17-dehydrolimonoate A-ring lactone via the 17-dehydrolimonoid pathway and bitter nomilin to nonbitter obacunone via the obacunone pathway.

THE BACTERIUM

The novel bacterium of this invention was isolated from the soil by enrichment with 3-furoic acid as a single carbon source and a mineral salt medium. The purified organism was classified as *Corynebacterium fascians* by the procedures of *Bergey's Manual of Determinative Bacteriology*, 8th Edition, Eds. Buchanan and Gibbons; Williams and Wilkins, Baltimore, MD (1974) and *Manual of Clinical Microbiology*, 2nd Edition, Eds. Linnette, Spaulding and Truent, American Society for Microbiology, Washington, D.C. (1974) and the use of API 20 E Gram negative bacteria identification system (Analytab Products, Plainview, N.Y.). A culture of the organism has been deposited in the Agricultural Research Culture Collection on (NRRL) in Peoria, Ill., 61604 and has been assigned the accession number B-15096. Samples of the strain may be obtained from the depository.

The strain NRRL B-15096 has the following characteristics: Colonies are circular, entire, convex, and orange-white color with colony diameter on nutrient agar 1–3 mm after 4 or more days. The cells are straight or club shaped $0.3–0.5 \times 1–3\mu$, gram positive, aerobic, grow at 37° C., and non-motile; no spores were detected. The cells are catalase positive, utilize citrate as the sole carbon source and have an active urease. Sugars on the API strip were negative but glucose, sucrose, lactose, and galactose were utilized and fructose was rapidly utilized and acid produced in fermentation tubes. The following tests were negative: beta-galatosidase, arginine dehydrolase, lysine decarboxylase, ornithine decarboxylase, tryptophane deaminase; acetoin, indol and $H_2S$ were not produced nor was gelatin liquefied.

PREPARATION OF THE BACTERIUM

The production of cells of the strain of *Corynebacterium fascians* having the characteristics of NRRL-B-15096 is carried out in an aqueous nutrient medium containing sources of carbon, nitrogen and inorganic salts assimilable by the bacterium. Examples of carbon sources include sugars such as fructose, galactose, glucose and sucrose. Growth is slow on the two latter sugars. When lactose is the sole carbon source in the medium, little or no growth occurs. As noted above, previously isolated limonoid-metabolizing bacteria require a limonoid-inducer such as limonoate in the medium to produce cells having limonoid-metabolizing enzymes. In contrast, the bacterium of the invention produces limonoid-metabolizing enzymes without exogenous induction, thus a limonoate substrate is not required in the medium, although it may be used if desired as the bacterium will utilize it as a growth substrate.

The nitrogen source in the medium may be provided by inorganic salts such as alkali metal nitrates, ammonium salts or organic substrates such as yeast hydrolysates, hydrolysates of casein, peptone, beef extract, primary yeast, corn steep liquor and the like.

Among the nutrient inorganic salts which can be incorporated into the culture medium are the customary salts capable of providing sodium, potassium, ammonium, phosphate, sulfate, nitrate and like ions and trace amounts of soluble compounds of magnesium, iron and manganese.

Production of the cells is effected under aerobic conditions at any temperature conductive to satisfactory growth of the organism i.e., from about 15° C. to 37° C.; the preferred temperature range is about 24° C. to 27° C. The pH of the nutrient media suitable for growing the *C. fascians* culture is about neutrality. Incubation time depends on the carbon source used in the medium and can be followed by measuring the optical density of the medium at 600 nm. When fructose is the carbon source, good growth occurs within 8 hours; however, in general, a growth time of at least about 40 hours is preferred. One may use conventional shake-flask techniques for small runs. For larger scale operation it is convenient to carry out the culture in a tank, applying agitation and aeration to the inoculated liquid medium. After incubation, the cells are harvested by conventional methods such as centrifugation or filtering. They may be used as is or frozen for later use.

USE OF THE BACTERIUM

The strain of *Corynebacterium fascians* having the characteristics of NRRL B-15096 is useful to reduce or eliminate bitterness in citrus products and by-products, particularly citrus juices. As stated previously, isolation of the debittering enzymes produced by the bacterium is not required prior to use for reducing or eliminating bitterness in citrus products.

*C. fascians* may be used in any of several ways to debitter citrus products. For example, a bacterial suspension may be used as free cells or placed in a dialysis sac. Another method is to immobilize the enzyme on a solid substrate. Many procedures and substrates to immobilize biologically active compounds for food processing are well known in the art can be used to treat *C. fascians*. For example, the bacteria can be constrained or held to a number of solid supports by adsorption, covalent attachment, crosslinking, entrapment, microencapsulation or by various combinations of the foregoing methods. Examples of enzyme supports include polysaccharide and substituted-polysaccharide materials such as agarose, DEAE-Sephadex, DEAE-cellulose, cellulose triacetate, chitin and chitosan; inorganic supports such as porous ceramic, porous glass and the like; fibrous proteins such as gelatin, collagen and keratin; synthetic polymers such as phenolic resins, phenol-formaldehyde resins and Dowex resins; hollow fibers; and hydrogels wherein a crosslinked polymer network is formed in the presence of the microbial cell so as to entrap the cells such as entrapment in polyacrylamide gels or poly(2-hydroxyethylmethacrylate) gels using a crosslinking agent such as N,N'-methylenebisacrylamide. For further information about immobilizing systems and substrates in food systems, see "Symposium: Immobilized Enzymes in Food Systems," by W. L. Stanley and A. C. Olson, *Journal of Food Science,* Volume 39, pp 660–666 (1974) and "Immobilized Enzymes" by A. C. Olson and R. A. Korus in *Enzymes in Food and Beverage Processing,* ACS Symposium Series No. 47, Ed. by Ory and Angelo, American Chemical Society, pp 100–131 (1974) which are hereby incorporated by reference. Use of immobilized bacterial cells to debitter limonoid-containing citrus is the method of choice for the following reasons: the cells are capable of repeated use resulting in increased efficiency and decreased effective cost; there is improved enzyme behavior, i.e., the enzyme system in the immobilized cells has a higher enzyme activity at juice pHs; there is increased stability of the enzyme in the immobilized cells; and there is no addition of free cells to the citrus juice thereby eliminating the presence of bacterial cells in the final product.

The invention is further demonstrated by the following illustrative examples. This is by way of illustration and not limitation.

EXAMPLE 1

Growth of *C. fascians* on various carbon sources

A mineral salt solution containing the following ingredients was prepared

| | | | |
|---|---|---|---|
| KH$_2$PO$_4$ | 0.20 gm. | Fe$_2$(SO$_4$)$_3$.6H$_2$O | 0.054 mg. |
| K$_2$HPO$_4$ | 0.15 gm. | (NH$_4$)P(Mo$_3$O$_{10}$)$_4$ | 0.024 mg. |
| NaH$_2$PO$_4$.H$_2$O | 2.00 gm. | ZnSO$_4$.7H$_2$O | 0.050 mg. |
| Na$_2$HPO$_4$ | 1.50 gm. | CuSO$_4$.5H$_2$O | 0.0025 mg. |
| NH$_4$NO$_3$ | 0.60 gm. | MnSO$_4$ | 0.0055 mg. |
| NaNO$_3$ | 3.80 gm. | H$_3$BO$_3$ | 0.057 mg. |
| MgSO$_4$.7H$_2$O | 0.30 gm. | H$_2$O | 1000 ml. |

Into a 2.8-liter Fernbach flask was placed 500 ml of a medium containing 0.2 percent nutrient broth (beef extract, 3 g/l; petone 5 g/l), 0.2 percent of the carbon source and the mineral salt solution. The medium was inoculated with 10 ml of a 48-hour culture of C. fascians NRRL B-15096. Incubation was at 25° C. on a shaker. Growth at various incubation times was measured by reading the optical density of the media at 600 nm. FIG. 1 shows the growth curves of the bacterium when fructose, sodium limonoate and galactose were used as the carbon sources.

EXAMPLE 2

Production of limonoate dehydrogenase by C. fascians grown on various carbon sources C. fascians NRRL B-15096 was grown as described in Example 1 with the exception that the carbon source was added to provide a concentration of 0.4 percent. After 48 hours of incubation, cells were collected by centrifugation at 5,000 g for 15 min, washed with 0.5 M potassium phosphate buffer at pH 7.0 and kept frozen until use.

Frozen cells were suspended in 50 ml of 0.1 M potassium phosphate buffer at pH 7.0 containing $10^{-3}$ M dithiothreitol and and disrupted in an ice bath with a Branson J-22 sonifier. The suspension was centrifuged at 20,000 g for 15 min and the supernatant was brought to 0.9 saturation with solid (NH$_4$)$_2$SO$_4$. The mixture was then centrifuged at 20,000 g for 15 min and the recovered precipitate was dissolved in a minimal portion of 0.1 M potassium phosphate buffer at pH 7.0 and used for enzyme analysis. Limonoate dehydrogenase activity was used for the estimation of the limonoid-metabolizing enzyme activity of the bacterial cells.

Enzyme assay method: Limonoate dehydrogenase activity was assayed by following the increase in absorbancy at 340 nm due to the formation of dihydronicotinamide adenine dinucleotide (NADH) from nicotinamide adenine dinucleotide (NAD) added to the reaction system as a hydrogen acceptor. In particular, activity was assayed in one ml of a reaction mixture containing 0.01 M Sodium limonoate, 0.1 M tris-(hydroxymethyl)aminomethane (Tris) buffer at pH 8.2 and $5\times10^{-4}$ M NAD and enzyme. The reaction was carried out at 25° C. in a standard silica gel cuvette with 1-cm light path. One unit of limonoate dehydrogenase activity is defined as the amount which catalyzes the production of 1 μmole of 17-dehydro metabolite per minute under the above conditions.

When cells were grown using limonoate, galactose or fructose as the carbon source, limonoate dehydrogenase was produced in all cases showing that the organism produces constitutive limonoid-metabolizing enzymes, that is, that a limonoid inducer is not required in the medium to produce cells which possess limonoid-metabolizing enzymes. Limonoate dehydrogenase activity was highest in cells grown on limonoate followed by galactose and fructose. The results are tabulated below:

| | | limonoate dehydrogenase | |
|---|---|---|---|
| carbon source | cell yields (g) | total activity (units) | activity/g cells (units) |
| limonoate | 3.22 | 7392 | 2296 |
| galactose | 2.20 | 2957 | 1344 |
| fructose | 2.06 | 1546 | 750 |

EXAMPLE 3

Comparison of enzyme activity of C. fascians grown without a limonoid inducer to limonoid-metabolizing bacteria grown with limonoate in the medium C. fascians NRRL B-15096 was grown as described in Example 2 using galactose as the carbon source. Ten ml of a 48-hour culture of the bacterium Arthrobacter globiformis (described in U.S. Pat. No. 3,911,103) was grown in 400 ml of a medium containing 1.0 percent sodium limonoate and the mineral salt solution described in Example 1. After incubation at 25° C. for 48 hours, limonoate dehydrogenase activity was measured. Ten ml of a 48-hour culture of Pseudomonas 321-18 (described in U.S. Pat. No. 3,920,851) was grown in 400 ml of a medium containing 0.4 percent sodium limonoate and the mineral salt solution described in Example 1. After incubation at 25° C. for 48 hours, limonoate dehydrogenase activity was measured.

C. fascians produced limonoate dehydrogenase activity equaling that of A. globiformis and greater than Pseudomonas 321-18. The results are tabulated below:

| Bacterium | Limonoate dehydrogenase Total Activity (units) |
|---|---|
| C. fascians NRRL B-15096 | 2957 |
| Arthrobacter globiformis | 3160 |
| Pseudomonas 321-18 | 332 |

EXAMPLE 4

Reduction of limonin content of citrus juice sera by C. fascians cells immobilized in acrylamide gel C. fascians NRRL B-15096 was grown on 500 ml of a mineral salt medium containing 0.2 percent fructose by the procedures described in the Example 1. Three and one half grams of cells were immobilized in acrylamide gel as follows: cells were suspended in 14 ml of physiological saline. To the suspension, acrylamide monomer (2.63 g) N,N'-methylenebisacrylamide (BIS) (140 mg), 5% β-dimethylaminopropionitrile (1.75 ml) and 2.5% potassium persulfate (1.75 ml) were added. The mixture was incubated at 40° C. for 15 minutes.

The resulting gel was blended gently with a Polytron and packed in a 2.0-cm diameter column. A 100-ml portion of the serum was passed through the column once at a rate of 100 ml/hr at room temperature. The column was then washed thoroughly with water and 0.05 M potassium phosphate buffer at pH 7.0. The combined effluents were acidified to pH 2.0 with 1 N HCl and extracted twice with 150 ml CH$_2$Cl$_2$. The combined extracts were evaporated to dryness, and the residue was dissolved in 1 ml of acetonitrile and used for analysis of limonoids by thin layer chromatography. The silica gel plates were developed with toluene-EtOH- H₂O-HOAc (200-45-15-1, upper layer). They were then sprayed with Ehrlich's reagent and exposed to HCl gas to reveal the limonoids as orange spots. The relative amounts of limonoids present were estimated visually by comparison with reference compounds. The controls were treated similarly with a column packed with acrylamide gel without bacterial cells.

These results show that *C. fascians* grown on fructose converts bitter limonin to nonbitter limonol in juice sera of navel orange, Valencia orange and grapefruit. This confirms the results shown in Example 2 that *C. fascians* produces constitutive enzymes for limonoid metabolism. The results are tabulated below:

| | Limonin content | |
|---|---|---|
| Juice sera | Control (ppm) | Treated (ppm) |
| Navel orange | 20.0 | 3.0 |
| | 23.0 | 4.0 |
| Valencia orange | 20.0 | 3.0 |
| | 23.0 | 3.0 |
| Grapefruit | 21.5 | 4.5 |
| | 19.5 | 4.0 |

EXAMPLE 5

Reduction of limonin content of navel orange juice serum by immobilized cells of *C. fascians* grown on limonoate

*C. fascians* NRRL B-15096 was grown on 500 ml of a 0.2% Na-limonoate-mineral salt medium by the procedure described in Example 1. Three and one half grams were immobilized in acrylamide gel, blended and packed in a 2.0-cm diameter column by the procedures as described in Example 4. One hundred ml of navel orange juice serum were treated with the column and compared to controls as described in Example 4. The enzyme system very effectively converted limonin to limonol in the sera. The system was used 10 times without losing its effectiveness. The results are tabulated below:

| | | Limonin content | |
|---|---|---|---|
| Runs | Days after immobilized | Control (ppm) | Treated (ppm) |
| 1 | 1 | 23 | 4.0 |
| 2 | 2 | 21 | 4.0 |
| 3 | 12 | 21 | 3.0 |
| 4 | 14 | 21 | 3.5 |
| 5 | 20 | 21 | 3.0 |
| 6 | 22 | 23 | 5.0 |
| 7 | 26 | 21 | 5.5 |
| 8 | 28 | 21 | 6.0 |
| 9 | 30 | 23 | 6.0 |
| 10 | 35 | 21 | 7.0 |

EXAMPLE 6

Reduction of nomilin content of navel and Valencia orange juice sera by *C. fascians* cells immobilized in acrylamide gel

*C. fascians* was grown on a 0.2% fructose-mineral salt medium as described in Example 1 and 3.5 g cells were immobilized in acrylamide gel by the procedures in Example 4. They were packed in a 2.0-cm diameter column. Eight hundred and fifty ml of navel orange juice serum containing 40 ppm of nomilin were treated with the column by the procedure in Example 4. Analysis of the treated serum showed that the nomilin content was reduced to 8.0 ppm. Similarly, 1,000 ml of Valencia orange juice serum containing 40 ppm of nomilin were treated with the same column. The nomilin content was reduced to 7.5 ppm. Analysis of metabolites showed that the major metabolite (over 90% of the total metabolites) was nonbitter obacunone showing that *C. fascians* cells grown on fructose also convert bitter nomilin to nonbitter obacunone.

EXAMPLE 7

Reduction of limonin content of navel orange juice serum by *C. fascians* cells grown on fructose The organism was grown on a 0.2% fructose-mineral salt medium as described in Example 1 and 4.0 g of cells were immobilized in acrylamide gel as described in Example 4. They were packed in a 2.0-cm diameter column. One hundred ml of the navel orange serum were passed through the column. The system was used 15 times. In each case the limonin content was substantially reduced. The results are tabulated below:

| | Limonin content | |
|---|---|---|
| Runs | Control (ppm) | Treated (ppm) |
| 1 | 21 | 4.0 |
| 2 | 21 | 3.5 |
| 3 | 21 | 4.4 |
| 4 | 23 | 4.5 |
| 5 | 23 | 3.5 |
| 6 | 23 | 5.0 |
| 7 | 21 | 6.0 |
| 8 | 21 | 6.5 |
| 9 | 23 | 6.0 |
| 10 | 23 | 6.5 |
| 11 | 21 | 7.0 |
| 12 | 21 | 7.5 |
| 13 | 21 | 8.0 |
| 14 | 23 | 8.0 |
| 15 | 23 | 10.0 |

Having thus described my invention, I claim:

1. A biologically pure culture of *Corynebacterium fascians* NRRL B-15096 which is further identified as having the capability of producing enzymes which convert bitter limonoids to nonbitter compounds without the presence of a limonoid inducer in the growth medium.

2. The culture of claim 1 wherein said bacterium is grown on a medium containing galactose.

3. The culture of claim 1 wherein said bacterium is grown on a medium containing fructose.

4. The culture of claim 1 wherein said bacterium is grown on a medium containing limonoate.

5. The process for reducing bitterness in limonoid-containing citrus products, which comprises contacting the citrus product with the bacterium *Corynebacterium fascians* NRRL B-15096 which is further identified as having the capability of producing enzymes which convert bitter limonoids to nonbitter compounds without the presence of a limonoid inducer in the growth medium.

6. The process of claim 5 wherein said bacterium comprises free cells.

7. The process of claim 5 wherein said bacterium is contained in a dialysis sac.

8. The process of claim 5 wherein said bacterium is immobilized on a solid substrate.

9. The process of claim 8 wherein said bacterium is immobilized in polyacrylamide.

10. The process of claim 5 wherein said citrus product is navel orange juice.

11. The process of claim 5 wherein said citrus product is Valencia orange juice.

12. The process of claim 5 wherein said citrus product is grapefruit juice.

13. The process of converting bitter limonoid components in limonoid-containing citrus juice to nonbitter compounds, which comprises contacting the citrus juice with the bacterium *Corynebacterium fascians* NRRL B-15096 which is further identified as having the capability of producing enzymes which convert bitter limonoids to nonbitter compounds without the presence of a limonoid inducer in the growth medium.

14. The process of claim 13 wherein said bitter component is limonin and said nonbitter compound is limonol.

15. The process of claim 13 wherein said bitter component is nomilin and said nonbitter compound is obacunone.

* * * * *